US009402585B2

(12) United States Patent  
Hatano et al.

(10) Patent No.: US 9,402,585 B2  
(45) Date of Patent: Aug. 2, 2016

(54) BIOLOGICAL INFORMATION MONITOR AND BIOLOGICAL INFORMATION MONITORING SYSTEM

(71) Applicant: NIHON KOHDEN CORPORATION, Tokyo (JP)

(72) Inventors: Yuka Hatano, Tokyo (JP); Naokatsu Ohta, Tokyo (JP); Kohei Ishikawa, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 170 days.

(21) Appl. No.: 14/171,064

(22) Filed: Feb. 3, 2014

(65) Prior Publication Data

US 2014/0218368 A1 Aug. 7, 2014

(30) Foreign Application Priority Data

Feb. 5, 2013 (JP) .................................. 2013-020869

(51) Int. Cl.
| | |
|---|---|
| G06T 11/20 | (2006.01) |
| A61B 5/00 | (2006.01) |
| G06F 3/147 | (2006.01) |
| G06F 19/00 | (2011.01) |
| G09G 5/37 | (2006.01) |

(52) U.S. Cl.
CPC ............... *A61B 5/742* (2013.01); *G06F 3/147* (2013.01); *G06F 19/3406* (2013.01); *G09G 5/37* (2013.01); *G09G 2380/08* (2013.01)

(58) Field of Classification Search
None
See application file for complete search history.

(56) References Cited

U.S. PATENT DOCUMENTS

| 5,347,452 A * | 9/1994 | Bay, Jr. .................. G06Q 40/04 340/4.5 |
| 5,722,999 A | 3/1998 | Snell |
| 6,097,399 A * | 8/2000 | Bhatt ..................... G09G 1/162 345/440 |
| 8,194,944 B2 | 6/2012 | Tivig et al. |
| 2007/0073169 A1 * | 3/2007 | Averina ............... A61B 5/0816 600/483 |
| 2009/0054743 A1 * | 2/2009 | Stewart .............. A61B 5/02055 600/301 |

(Continued)

FOREIGN PATENT DOCUMENTS

| CN | 101862181 A | 10/2010 |
| CN | 102058404 A | 5/2011 |

(Continued)

OTHER PUBLICATIONS

The extended European Search Report for the related European Patent Application No. 14153759.7 dated May 21, 2014.

(Continued)

*Primary Examiner* — Ryan R Yang  
(74) *Attorney, Agent, or Firm* — Kenealy Vaidya LLP

(57) ABSTRACT

A biological information monitor includes: a displaying section on which a biological information display screen is displayed, the biological information display screen including a first display region on which a trend graph of first biological information is displayed and a second display region on which a histogram of second biological information is displayed; and a display controlling section which is configured to control contents displayed on the biological information display screen, and which is configured to cause the trend graph for a plurality of days and the histogram for the plurality of days to be simultaneously displayed in the first display region and the second display region, respectively.

4 Claims, 4 Drawing Sheets

(56) References Cited

U.S. PATENT DOCUMENTS

| | | | |
|---|---|---|---|
| 2009/0082640 A1* | 3/2009 | Kovach | A61B 5/04001 600/300 |
| 2009/0147006 A1 | 6/2009 | Buck et al. | |
| 2009/0171169 A1 | 7/2009 | Nagata | |
| 2011/0184752 A1* | 7/2011 | Ray | G06Q 50/22 705/2 |
| 2012/0197146 A1 | 8/2012 | Tan et al. | |
| 2013/0246089 A1 | 9/2013 | Gross et al. | |

FOREIGN PATENT DOCUMENTS

| | | |
|---|---|---|
| CN | 102622501 A | 8/2012 |
| JP | 2002-102362 A | 4/2002 |
| JP | 2003-559 A | 1/2003 |
| JP | 2006-318405 A | 11/2006 |
| JP | 2008-206553 A | 9/2008 |
| JP | 2009-153645 A | 7/2009 |
| JP | 2011-147784 A | 8/2011 |
| WO | 2012/017342 A1 | 2/2012 |

OTHER PUBLICATIONS

Chinese Office Action for the related Chinese Patent Application No. 201410045240.3 dated Feb. 15, 2016.

Japanese Office Action for the related Japanese Patent Application No. 2013-020869 dated Mar. 29, 2016.

* cited by examiner

BIOLOGICAL INFORMATION MONITOR AND BIOLOGICAL INFORMATION MONITORING SYSTEM

CROSS-REFERENCE TO RELATED APPLICATION(S)

This application is based upon and claims the benefit of priority from prior Japanese patent application No. 2013-020869, filed on Feb. 5, 2013, the entire contents of which are incorporated herein by reference.

BACKGROUND

The presently disclosed subject matter relates to a biological information monitor and biological information monitoring system for displaying biological information acquired from a subject.

As an apparatus for displaying biological information acquired from a subject on a display screen, many apparatus having varied display modes have been proposed. For example, a monitoring apparatus has been proposed in which trend data related to a number of acquired biological information are displayed, or biological information for preset several hours is analyzed and the obtained data are displayed in the form of a histogram.

JP-A-2003-000559 discloses a biological information recording apparatus in which respiratory information and electrocardiogram information are output so as to be recorded in the same page, and the two kinds of information are vertically juxtaposed in the same time scale, thereby enabling the correlation between them to be grasped.

In the biological information recording apparatus disclosed in JP-A-2003-000559, however, respiratory information and electrocardiogram information are displayed in the unit of several tens of minutes to several hours. Therefore, the condition change of the patient in a long span cannot be grasped, and it is difficult to rapidly check whether the patient is on the way to recovery, stays the same, or becomes worse.

SUMMARY

The presently disclosed subject matter may provide a biological information monitor and biological information monitoring system in which the condition change of the patient in a long span can be checked rapidly and easily.

The biological information monitor may comprise: a displaying section on which a biological information display screen is displayed, the biological information display screen including a first display region on which a trend graph of first biological information is displayed and a second display region on which a histogram of second biological information is displayed; and a display controlling section which is configured to control contents displayed on the biological information display screen, and which is configured to cause the trend graph for a plurality of days and the histogram for the plurality of days to be simultaneously displayed in the first display region and the second display region, respectively.

The first biological information may be identical with the second biological information.

The first biological information may be different from the second biological information.

There may be provided the biological information monitoring system in which a plurality of the biological information monitors, and a central monitor which is configured to centrally manage the biological information monitors are connected to one another via a network, wherein the trend graph and histogram which are displayed on an arbitrary one of the biological information monitors are displayed on the central monitor in a same display mode as in the biological information monitor.

DETAILED DESCRIPTION OF EXEMPLARY EMBODIMENTS

Hereinafter, an embodiment of the biological information monitor and biological information monitoring system of the presently disclosed subject matter will be described with reference to the accompanying drawings.

Figure 1:
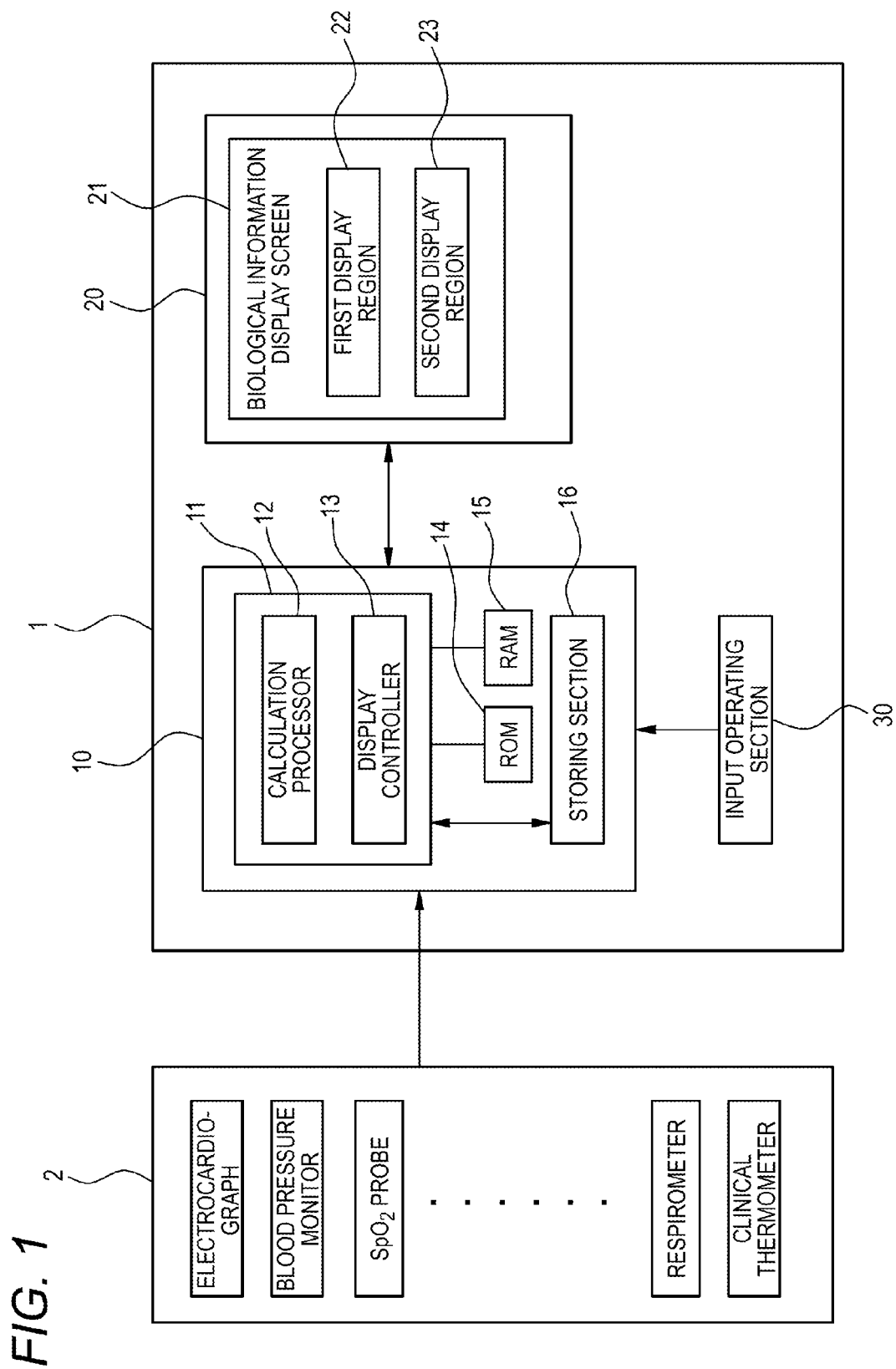
FIG. 1 is a block diagram illustrating the configuration of the biological information monitor of the presently disclosed subject matter.

FIG. 1 is a diagram illustrating the configuration of a biological information monitor 1. The biological information monitor 1 is an apparatus which calculates biological information acquired from the subject (patient), and which displays results of calculation processes. The biological information monitor 1 can be used as a bedside monitor which is disposed for each patient, or a central monitor which manages a plurality of bedside monitors connected to a network.

The biological information monitor 1 is connected to a biological information acquiring unit 2 for acquiring biological information such as an electrocardiogram, the heart rate (pulse rate), the blood pressure, the arterial oxygen saturation, the percutaneous oxygen saturation, the suction oxygen concentration, the respiration, and the body temperature. As shown in FIG. 1, specific examples of the biological information acquiring unit 2 are various devices (sensors) such as an electrocardiograph, a blood pressure monitor, an SpO2 probe, a respirometer, and a clinical thermometer. The biological information acquiring unit 2 is attached to the subject, and biological information acquired by the biological information acquiring unit 2 is input to the biological information monitor 1.

The biological information monitor 1 may include: a controller 10 which controls the operation of the monitor; a displaying section 20 which displays the measured biological information; and an input operating section 30 through which an operation signal related to biological information is input from the outside. The biological information acquired by the biological information acquiring unit 2 is input to the controller 10 of the biological information monitor 1.

The controller 10 includes a CPU (Central Processing Unit) 11 as a main component, and controls the operations of the sections of the biological information monitor 1 based on information which is supplied from the biological information acquiring unit 2 and the input operating section 30. The controller 10 further may include a storing section 16 which stores biological information acquired by the biological information acquiring unit 2.

The CPU 11 performs various numerical calculations, information processing, and the like in accordance with programs stored in a ROM 14, and controls the operation of the biological information monitor 1. The CPU 11 uses a RAM 15 as a region for storing various data.

The CPU 11 may include a calculation processor 12 and a display controller 13. The CPU 11 functions as the calculation processor 12 and the display controller 13 to perform numerical calculations, information processing, controlling of a screen display, and the like.

The calculation processor 12 analyzes biological information signals acquired by the biological information acquiring unit 2, and performs calculation processes. Specifically, the calculation processor 12 performs calculation processes on the acquired biological information to produce data (trend data) indicating the temporal change of the biological information. Moreover, the calculation processor 12 statistically processes each of the kinds of the acquired biological information to produce an integral value (histogram data) indicating the frequency distribution of the information. The trend data may be waveform data such as an electrocardiogram waveform, a pulse waveform, an SpO2 (oxygen saturation) waveform, and a respiratory volume waveform. As the histogram data, data indicating the frequency distribution which is produced based on these waveform data may be used.

The calculation processor 12 produces trend data and histogram data at daily intervals (on a day-to-day basis). Namely, the trend data and histogram data are produced in units of measured data over continuous 24 hours. The data which are produced for each day are continuously produced over a plurality of days. For example, the data are produced over at least two days or more, and preferably over one week, two weeks, or the like. The trend data and histogram data which are produced by the calculation processor 12 are stored in the storing section 16.

The display controller 13 causes the biological information acquired by the biological information acquiring unit 2, the trend data and histogram data which are produced by the calculation processor 12, and the like to be displayed on the displaying section 20. The display controller 13 reads out the trend data, the histogram data, and the like from the storing section 16, and causes the data to be displayed on the displaying section 20. The display controller 13 transmits a control signal for controlling the display contents, to the displaying section 20. The trend data are displayed on the displaying section 20 in the form of a trend graph, and the histogram data are displayed on the displaying section 20 in the form of a histogram. Based on the daily data which are produced as described above, the trend graph and histogram which are produced at daily intervals and over a plurality of days (for example, at least two days or more, and preferably one week, two weeks, or the like) are displayed.

In accordance with instructions (selection) which are externally input through the input operating section 30, the display controller 13 reads out information contents of which correspond to the instructions, from the storing section 16, and controls the displaying section 20 to display the information.

Based on the control of the CPU 11, the storing section 16 stores data of the acquired biological information or analysis data thereof. Namely, the storing section 16 stores the biological information acquired by the biological information acquiring unit 2, as data corresponding to itself, or in the form of the trend data and histogram data which are produced by the calculation processor 12. The storing section 16 stores these data at daily intervals, and continuously the daily data over a plurality of days (for example, at least two days or more, and preferably one week, two weeks, or the like). The storing section 16 further stores individual data of the patient such as the name, the gender, the age, and the date when the measurement is started (time and date of admission). As the storing section 16, for example, a disk such as a DVD, or a semiconductor memory such as a memory card may be used.

Based on the control signal transmitted from the display controller 13, the displaying section 20 displays the measured biological information. The displaying section 20 may be configured by, for example, an LCD or an organic EL panel, and includes a biological information display screen 21 for displaying biological information. The biological information display screen 21 may include a first display region 22 for displaying a trend graph of biological information, and a second display region 23 for displaying a histogram of biological information.

The biological information display screen 21 can display plural kinds of measured biological information. The biological information display screen 21 may include a plurality of display regions each for displaying a trend graph, and a plurality of display regions each for displaying a histogram. The screen is configured so that the positions of the trend graph display regions and the histogram display regions can be changed by external designation through the input operating section 30.

The input operating section 30 may be a keyboard, a mouse, a touch panel. The input operating section 30 is connected to the controller 10, and, based on an input operation from the outside (medical person), transmits an operation signal for designating biological information which is to be displayed on the biological information display screen 21, to the controller 10. Specifically, the medical person can perform selection of biological information which is to be displayed on the biological information display screen 21, that of biological information which is to be displayed in the first display region 22 as a trend graph, that of biological information which is to be displayed in the second display region 23 as a histogram, etc.

A trend graph of biological information which is selected by the medical person from the measured biological information is displayed in the first display region 22, and, at the same time, a histogram of the selected biological information is displayed in the second display region 23.

Next, biological information to be displayed on the biological information display screen 21 of the displaying section 20 will be described with reference to FIGS. 2 and 3.

Figure 2:
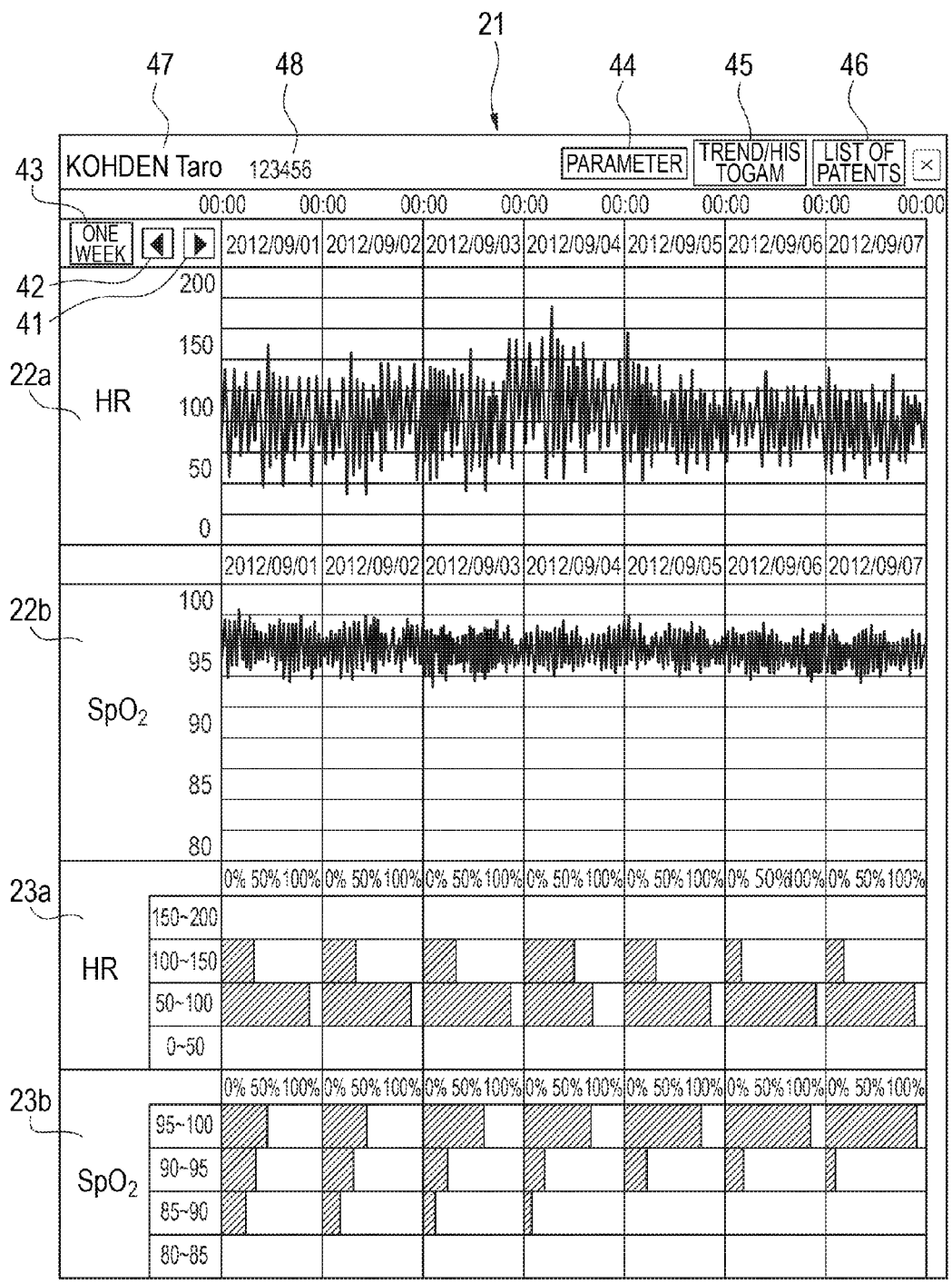
FIG. 2 is a view illustrating an example of trend graphs and histograms which are displayed on a display screen of the biological information monitor.

FIG. 2 is a view illustrating an example of trend graphs of biological information and histograms thereof, and shows a case where the kinds of the biological information displayed as the trend graphs are identical with those of the biological information displayed as the histograms.

As shown in FIG. 2, the biological information display screen 21 is divided into vertical four stages or display regions 22a, 22b, 23a, 23b, trend graphs of biological information are displayed in the upper two stages or the display regions 22a, 22b, and histograms of the biological information are displayed in the lower two stages or the display regions 23a, 23b. The upper two stages or the display regions 22a, 22b in each of which a trend graph is displayed correspond to the first display region 22 which has been described with reference to FIG. 1, and the lower two stages or the display regions 23a, 23b in each of which a histogram is displayed correspond to the second display region 23. The number of stages which are obtained by dividing the display regions is not limited to four.

In the embodiment, the HR (heart rate) and the SpO2 (oxygen saturation) are selected as biological information to be displayed. A trend graph of the HR is displayed in the display region 22a, and a histogram of the HR is displayed in the display region 23a. A trend graph of the SpO2 is displayed in the display region 22b, and a histogram of the SpO2 is displayed in the display region 23b. From the trend graphs, it is possible to surely detect dispersions and acute changes of the HR and the SpO2. From each of the histograms, it is possible to determine rapidly and easily the degree in which the measured value changes during one day, and the mode value of the biological information. The condition change of the subject can be determined by checking the mode value.

In each of the display regions 22a, 22b, 23a, 23b, a trend graph or histogram of biological information which has been measured at daily intervals (on a day-to-day basis) over a plurality of days are continuously displayed. Specifically, trend graphs and histograms of the heart rate and oxygen saturation which have been measured at daily intervals (from 00:00 to 24:00) in one week of from 2012 Sep. 1 to 2012 Sep. 7 are displayed in a span of one day. The days (from 2012 Sep. 1 to 2012 Sep. 7) of one week over which to-be-displayed biological information is measured (hereinafter, such days are referred to as display days) can be changed. For example, the display days can be changed forward or backward by pressing (touching) a forward button 41 or back button 42 displayed on the biological information display screen 21.

Moreover, the display period (number of display days) of biological information can be externally set and changed through the input operating section 30. When a period setting button 43 displayed on the biological information display screen 21 is pressed, for example, selection candidates (one day, one week, two weeks, and the like) for the display period are displayed. When one of the selection candidates is designated, the display period can be changed to the designated one. In this example, in the case where the display period is changed, the display periods of the trend graphs and the histograms are simultaneously changed to the changed display period. Namely, the trend graphs and the histograms are always displayed over the same display span in a comparative manner.

The kinds of biological information which is to be displayed on the biological information display screen 21 can be externally set and changed through the input operating section 30. When a parameter button 44 displayed on the biological information display screen 21 is pressed, for example, selection candidates (the blood pressure, the respiratory rate, and the like) for biological information are displayed. When one of the selection candidates is designated, the displayed biological information can be changed to the designated one.

The display mode (the display of trend graphs or histograms) of biological information which is to be displayed on the biological information display screen 21 can be externally set and changed through the input operating section 30. When a trend/histogram button 45 displayed on the biological information display screen 21 is pressed, for example, the display mode of biological information which is to be displayed on the biological information display screen 21 can be changed from trend graphs to histograms (or from histograms to trend graphs).

The subject displayed on the biological information display screen 21 can be externally set and changed through the input operating section 30. When a patient list button 46 displayed on the biological information display screen 21 is pressed, for example, a list of the names of subjects is displayed. When one of the subject names is designated, biological information of the designated subject can be displayed on the biological information display screen 21. The name of the designated subject is displayed in a subject name display region 47. An ID which is given correspondingly with the name of the subject is displayed in an identification code region 48.

Figure 3:
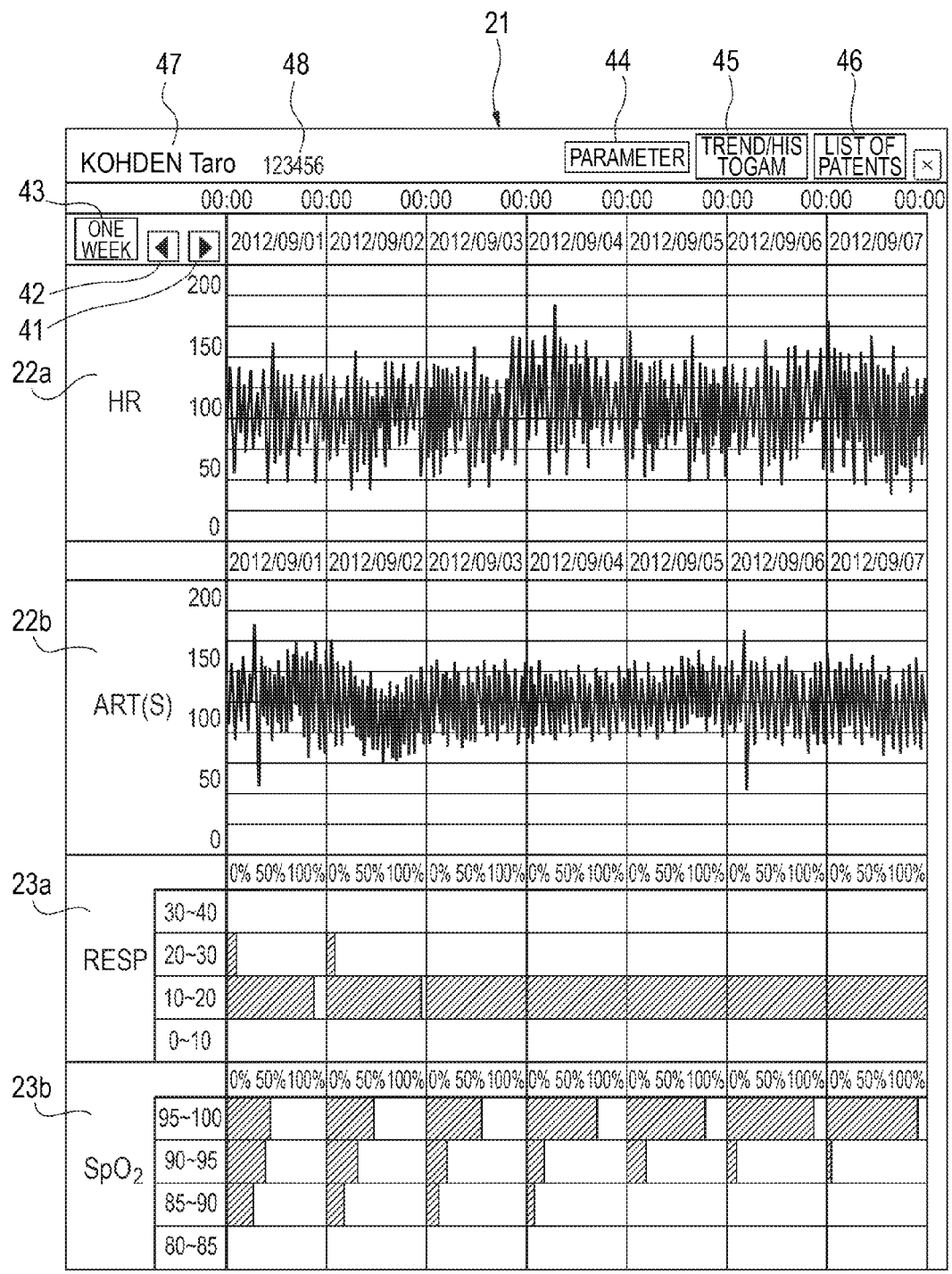
FIG. 3 is a view illustrating a modification of trend graphs and histograms which are displayed on the display screen of the biological information monitor.

FIG. 3 is a view illustrating a modification. The modification is different from the example shown in FIG. 2 in that biological information displayed as a trend graph is different from that displayed as a histogram. In the modification shown in FIG. 3, trend graphs and histograms of different kinds of biological information are simultaneously displayed on the biological information display screen 21. In the following description of the modification, components which are identical with or similar to those of the example shown in FIG. 2 are denoted by the same reference numerals, and their detailed description is omitted.

As shown in FIG. 3, trend graphs of biological information are displayed in the upper two stages or the display regions 22a, 22b of the biological information display screen 21, and histograms of biological information are displayed in the lower two stages or the display regions 23a, 23b. As the kinds of biological information, four kinds, i.e., the HR (heart rate), the ART (S) (blood pressure), the RESP (respiratory rate), and the SpO2 (oxygen saturation) are selected. Then, a trend graph of the HR is displayed in the display region 22a, and that of the ART(S) is displayed in the display region 22b. Moreover, a histogram of the RESP is displayed in the display region 23a, and that of the SpO2 is displayed in the display region 23b.

The display modes (the displays of trend graphs and histograms) of biological information which is to be displayed on the biological information display screen 21 can be changed to each other by, for example, pressing the trend/histogram button 45 displayed on the biological information display screen 21.

When the trend/histogram button 45 is pressed after "HR" or "ART(S)" in the display region 22a or 22b where a trend graph is displayed as shown in FIG. 3 is designated by means of a predetermined designation button, for example, the display mode (trend graph) of the designated display region can be changed to the display of a histogram. When the trend/histogram button 45 is pressed once more in the changed display mode, the display mode can be returned (changed) to that of a trend graph.

The related contents which, when another one of the buttons displayed on the biological information display screen 21 is pressed, can be set and changed are identical with those of the example shown in FIG. 2.

Figure 4:
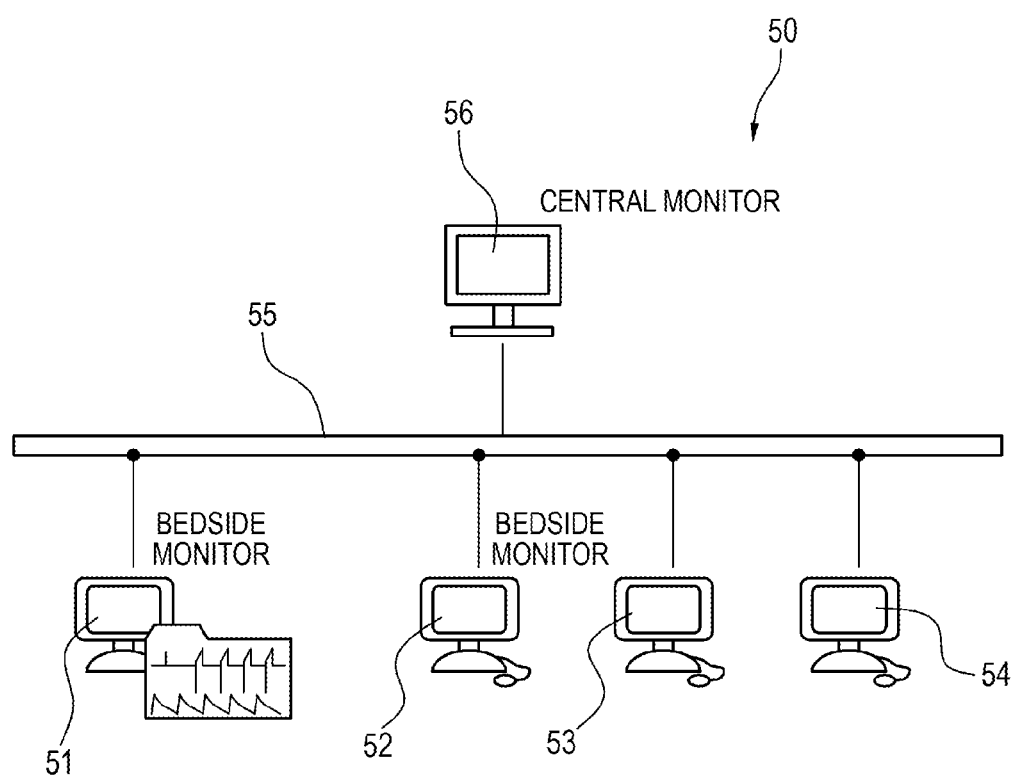
FIG. 4 is a diagram illustrating the configuration of the biological information monitoring system of the presently disclosed subject matter.

FIG. 4 is a diagram illustrating the configuration of a biological information monitoring system 50. The biological information monitoring system 50 may include a plurality of biological information monitors (bedside monitors) 51 to 54 and central monitor 56 which are connected to one another via a network 55.

The central monitor 56 is disposed in a nurse's station or the like, and can centrally monitor biological information of subjects. All kinds of information which is displayed on the bedside monitors 51 to 54 are transmitted to the central monitor 56 via the network 55. In the biological information monitoring system 50, the central monitor 56 functions as the above-described biological information monitor 1. On the central monitor 56, therefore, trend graphs and histograms of biological information can be displayed in the same display mode as in the above-described biological information monitor 1. On the central monitor 56, moreover, trend graphs and histograms of biological information of the subject who is designated by the medical person from the subjects (bedside monitors 51 to 54) connected to the network 55 can be displayed.

According to the configuration of the embodiment described above, a trend graph which indicates the dispersion (amplitude) of biological information, and a histogram which indicates the mode value that is a result of a statistical process are simultaneously displayed in the first and second display regions 22, 23 of the biological information display screen 21 in a long daily span, the trend graph and the histogram being produced over a plurality of days (for example, one week). Therefore, the dispersion and mode value of the biological information can be simultaneously checked, and mutual determination can be performed. Consequently, it is possible to check rapidly and easily the condition change of the patient, i.e., whether the patient is on the way to recovery, stays the same, or becomes worse.

When the same biological information is displayed in the forms of a trend graph and a histogram, it is possible to determine more correctly the condition change of the patient.

When different kinds of biological information are displayed in the forms of a trend graph and a histogram, biological information can be displayed in the optimum display mode corresponding to the biological information to be displayed. Therefore, it is possible to correctly determine the condition of the patient.

When trend graphs and histograms of patients (bedside monitors) are simultaneously displayed on the central monitor 56 connected to the network, in a long daily span, the trend graphs and the histograms being produced over a plurality of days, a medical person can easily check the condition changes of the patients without visiting to the respective patients. Therefore, central management can be conducted.

Although the presently disclosed subject matter has been described in detail and with reference to the specific embodiment, it is obvious to those skilled in the art that various changes and modifications can be made without departing from the spirit and scope of the presently disclosed subject matter. For example, respective ones of the trend graphs and histograms which are displayed on the screen may show common biological information (SpO2), and the other trend graph and the other histogram may show different kinds of biological information (HR and RESP), respectively.

According an aspect of the presently disclosed subject matter, a trend graph which indicates the dispersion of biological information, and a histogram which indicates the mode value are simultaneously displayed, the trend graph and the histogram being produced over a plurality of days, and therefore the condition change of the patient can be checked rapidly and easily.

What is claimed is:

1. A biological information monitor comprising:
    a displaying section on which a biological information display screen is displayed, the biological information display screen including a first display region on which a trend graph of first biological information is displayed and a second display region on which a histogram of second biological information is displayed; and
    a display controlling section which is configured to control contents displayed on the biological information display screen, the display controlling section which is configured to cause the trend graph and the histogram to be simultaneously displayed, and which is configured to cause the trend graph for a plurality of days and the histogram for the plurality of days to be displayed in the first display region and the second display region, respectively.

2. The biological information monitor according to claim 1, wherein the first biological information is identical with the second biological information.

3. The biological information monitor according to claim 1, wherein the first biological information is different from the second biological information.

4. A biological information monitoring system in which a plurality of the biological information monitors according to claim 1, and a central monitor which is configured to centrally manage the biological information monitors are connected to one another via a network, wherein
    the trend graph and histogram which are displayed on an arbitrary one of the biological information monitors are displayed on the central monitor in a same display mode as in the biological information monitor.

* * * * *